(12) United States Patent
Taylor et al.

(10) Patent No.: US 8,815,860 B2
(45) Date of Patent: Aug. 26, 2014

(54) METHODS FOR PREVENTING OXIDATIVE STRESS INJURY OF A TISSUE BY A FOLATE-TEMPOL CONJUGATE

(75) Inventors: W. Robert Taylor, Stone Mountain, GA (US); Sarah F. Knight, Atlanta, GA (US); Niren Murthy, Atlanta, GA (US); Kousik Kundu, Atlanta, GA (US)

(73) Assignees: Emory University, Atlanta, GA (US); Georgia Tech Research Corporation, Atlanta, GA (US)

( * ) Notice: Subject to any disclaimer, the term of this patent is extended or adjusted under 35 U.S.C. 154(b) by 0 days.

(21) Appl. No.: 13/497,398

(22) PCT Filed: Sep. 21, 2010

(86) PCT No.: PCT/US2010/049642
§ 371 (c)(1),
(2), (4) Date: Mar. 21, 2012

(87) PCT Pub. No.: WO2011/037913
PCT Pub. Date: Mar. 31, 2011

(65) Prior Publication Data
US 2012/0302575 A1 Nov. 29, 2012

Related U.S. Application Data (60) Provisional application No. 61/245,439, filed on Sep. 24, 2009.

(51) Int. Cl.
*C07D 401/10* (2006.01)
*C07D 475/08* (2006.01)
*A61K 31/519* (2006.01)
*A61K 31/445* (2006.01)

(52) U.S. Cl.
USPC .......................................... 514/249; 544/259

(58) Field of Classification Search
USPC .......................................... 544/259; 514/249
See application file for complete search history.

*Primary Examiner* — Bruck Kifle
(74) *Attorney, Agent, or Firm* — Emory Patent Group (57) ABSTRACT

The present disclosure is generally related to methods of preventing oxidative stress injury induced by renal ischemia-reperfusion by a Folate-TEMPOL conjugate.

6 Claims, 8 Drawing Sheets

METHODS FOR PREVENTING OXIDATIVE STRESS INJURY OF A TISSUE BY A FOLATE-TEMPOL CONJUGATE

CROSS REFERENCE TO RELATED APPLICATIONS

This application claims priority to PCT/US2010/049642 filed 21 Sep. 2010 and U.S. Provisional Application 61/245,439 filed on 24 Sep. 2009, which applications are hereby incorporated by this reference in their entireties.

ACKNOWLEDGEMENTS

This invention was made with government support under Grant HL080711 awarded by National Institutes of Health. The government has certain rights in the invention.

TECHNICAL FIELD

The present disclosure is generally related to methods of preventing oxidative stress injury induced by renal ischemia-reperfusion by a Folate-TEMPOL conjugate

SUMMARY

The present disclosure encompasses compositions and therapeutic methods for the prevention of oxidative stress injury that arises from ischemia and reperfusion of tissues. The compositions of the present disclosure may also be useful in preventing such injury that arises from other causes and stress to tissues, and may be useful in treating damaged tissues to enhance or initiate repair of the injury.

One aspect of the disclosure, therefore, encompasses methods for reducing oxidative stress injury of a tissue comprising: delivering to a human or animal subject a pharmaceutically acceptable composition comprising an effective amount of a Folate-TEMPOL conjugate, thereby reducing oxidative stress injury to a tissue.

In embodiments of this aspect of the disclosure, the pharmaceutically acceptable composition may further comprise a pharmaceutically acceptable carrier.

In some embodiments of the methods of this aspect of the disclosure, the oxidative stress injury to a tissue of the subject animal or human can be caused by renal ischemia.

In some embodiments of this aspect of the disclosure, the oxidative stress injury to a tissue of the animal or human subject can be caused by ischemia-reperfusion on a kidney.

In some embodiments of the methods of this aspect of the invention, the pharmaceutically acceptable composition may be delivered to the human or animal subject before the induction of oxidative stress injury to a tissue.

In some embodiments of the methods of this aspect of the invention, the pharmaceutically acceptable composition is delivered to the human or animal subject before a renal ischemia or the reperfusion thereof.

In embodiments of the methods of this aspect of the invention, the Folate-TEMPOL conjugate has the formula:

or salts or prodrugs thereof.

Another aspect of the disclosure encompasses compositions comprising a pharmaceutically active Folate-TEMPOL conjugate, wherein the Folate-TEMPOL conjugate has the formula:

In some embodiments of this aspect of the disclosure, the composition may further comprise a pharmaceutically acceptable carrier.

BRIEF DESCRIPTION OF THE FIGURES

Further aspects of the present disclosure will be more readily appreciated upon review of the detailed description of its various embodiments, described below, when taken in conjunction with the accompanying drawings.

The drawings are described in greater detail in the description and examples below.

Figure 1:
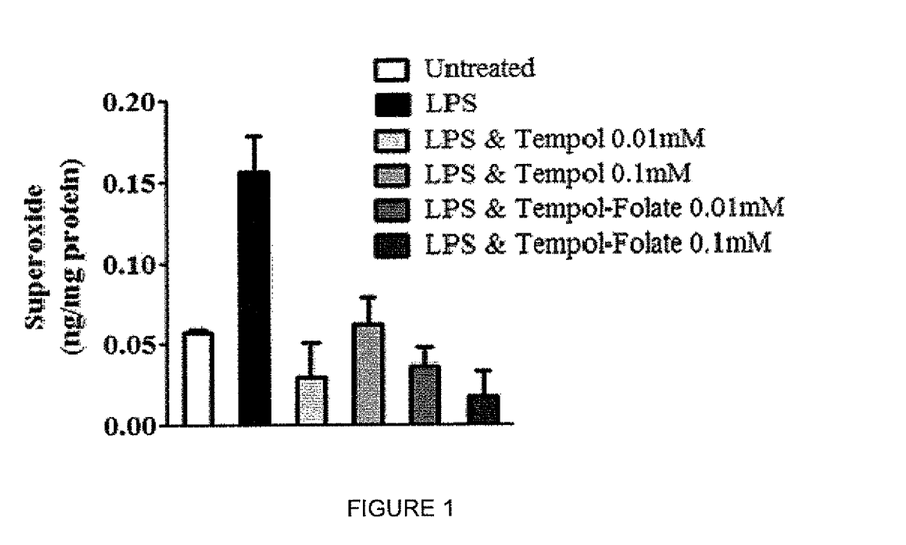
FIG. 1 shows data on superoxide concentration in cultured HK-2 cells measured by DHE-HPLC (n=3) between untreated and LPS treated mice. Tempol and tempol-folate incubation effectively scavenged superoxide production compared with LPS treated cells. Superoxide concentration was normalized to protein concentration. Data represent mean and SEM. This data provides evidence that folate conjugation with tempol does not affect the ability of tempol to scavenge superoxide.
Figure 2:
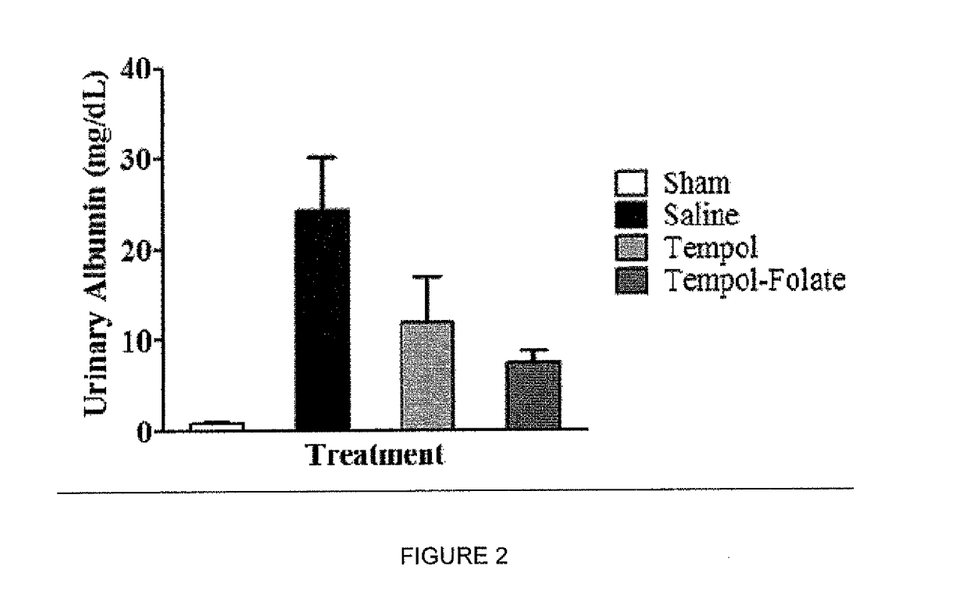
FIG. 2 shows data on urinary albumin excretion measured in urine samples taken over 24 hours from C57bl/6J mice comparing albumin excretion in saline treated mice with sham treated mice, n=8-14 and comparing tempol-folate treated mice with saline treated mice, n=8-14. Samples were collected 48 hours following 30 minute bilateral renal ischemia-reperfusion. Data represent mean and SEM. These data support the hypothesis that tempol-folate prevents kidney injury more effectively than free tempol in ischemia-reperfusion injury.
Figure 3:
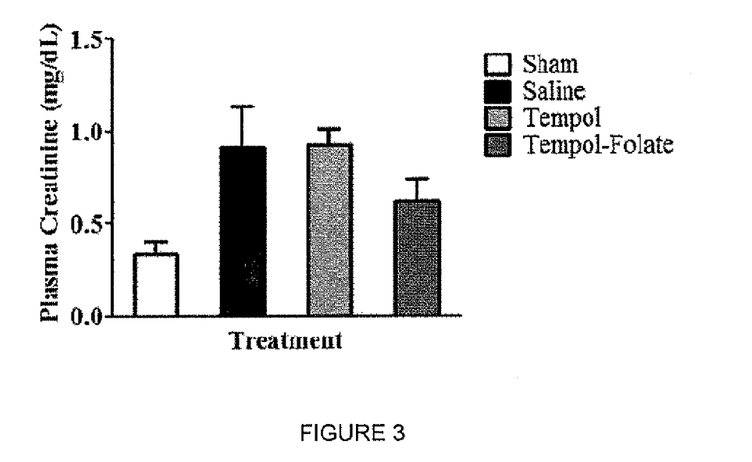
FIG. 3 shows plasma creatinine levels measured 48 hours following 30 minute bilateral renal ischemia-reperfusion of plasma creatinine in saline and tempol treated mice with sham mice, n=7-14. Data represent mean and SEM. These data indicate that tempol-folate preserves glomerular filtration rate from ischemia-reperfusion more effectively than unconjugated tempol.
Figure 4:
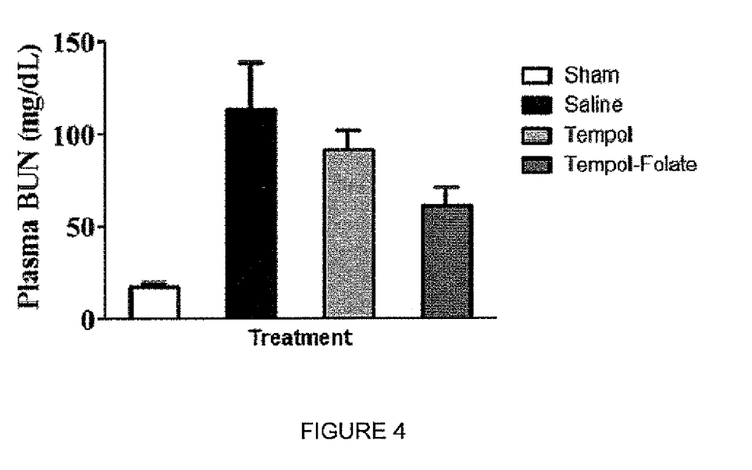
FIG. 4 shows data on plasma blood urea nitrogen (BUN) in saline treated mice with sham treated mice, n=7-14 and in saline treated mice and tempol treated mice. BUN was measured 48 hours following 30 minutes bilateral renal ischemia-reperfusion. Data represent mean and SEM. These data show that the proximal tubule function is protected from ischemic injury by tempol-folate compared with free tempol.
Figure 5A:
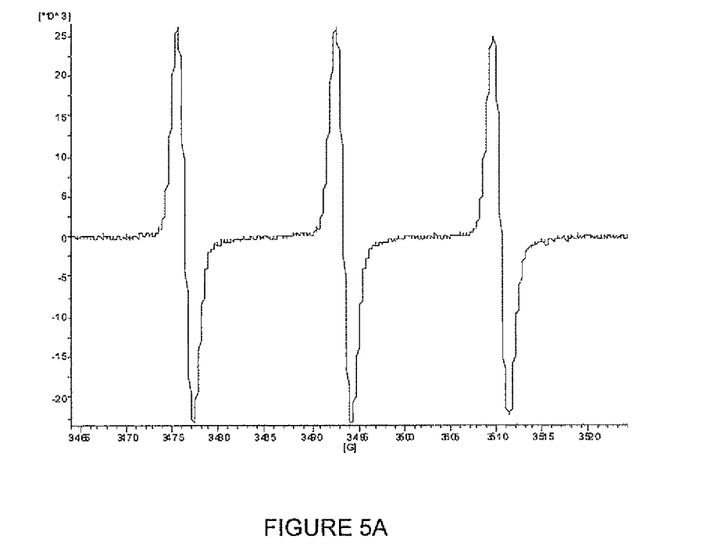
FIG. 5A shows a representative electron spin resonance plot produced by tempol.
Figure 5B:
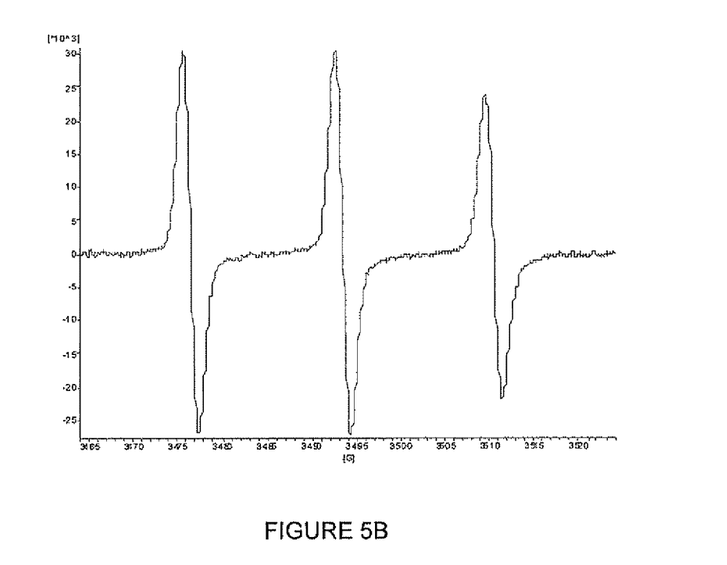
FIG. 5B shows a representative plot from tempol-folate conjugate.
Figure 5C:
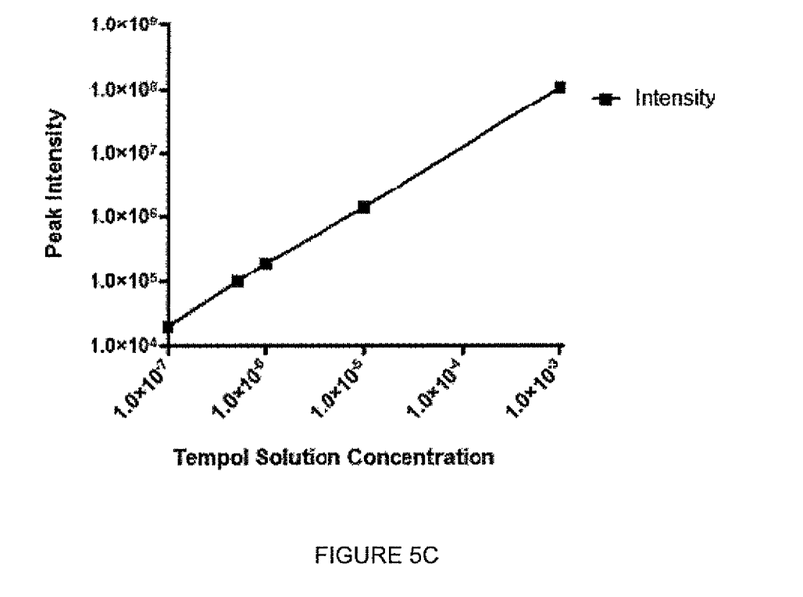
FIG. 5C shows a tempol standard curve measured by ESR.
Figure 5D:
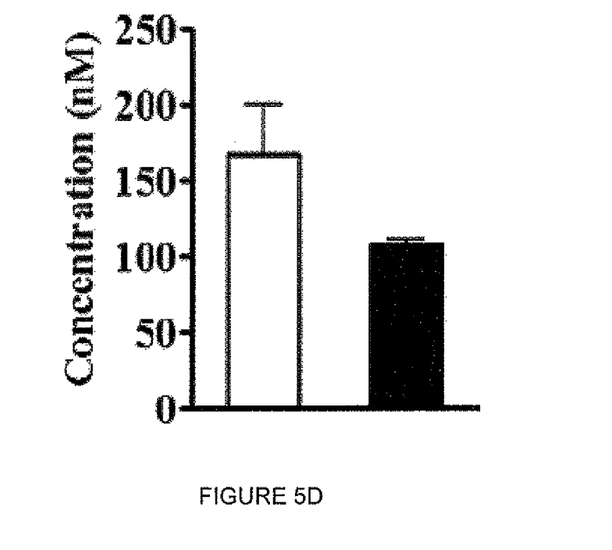
FIG. 5D shows supernatant tempol and tempol-folate concentration after incubation with human proximal tubule (HK-2) cells quantified by electron spin resonance (ESR).
Figure 5E:
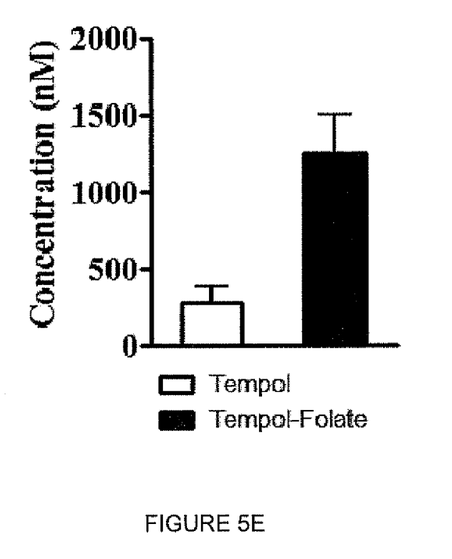
FIG. 5E shows HK-2 cell concentration of tempol and tempol-folate quantified by ESR.
Figure 5F:
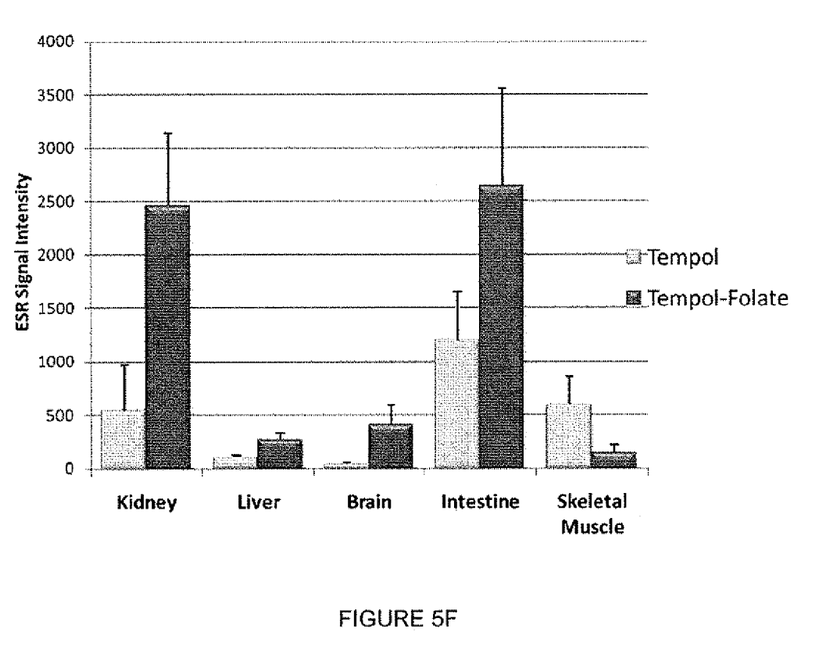
FIG. 5F shows data on tissue tempol and tempol-folate concentration quantified by ESR in mice after 48 hour intravenous infusion. Data represent mean and SEM. These data display that tempol-folate becomes more concentrated in cultured proximal tubule cells and in vivo in kidneys of mice compared with tempol indicating that folate conjugation leads to greater uptake into the cell, specifically in tissues rich with folate receptors such as the intestines and the kidney.
Figure 6A:
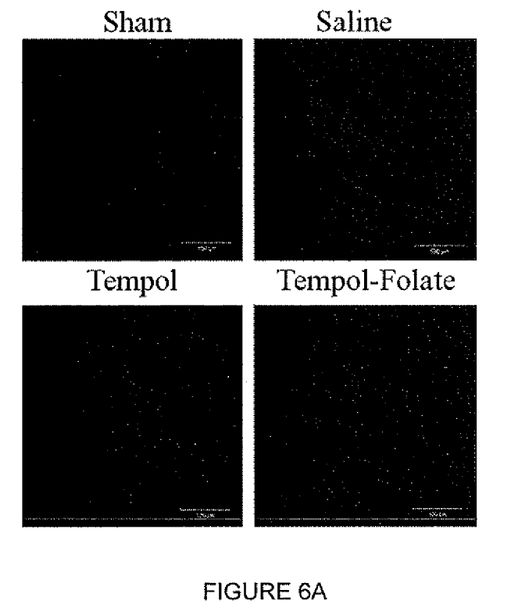
FIG. 6A shows representative images of mouse kidneys 2 hours post-ischemia incubated with hydrocyanine-3, images taken at 20× magnification.
Figure 6B:
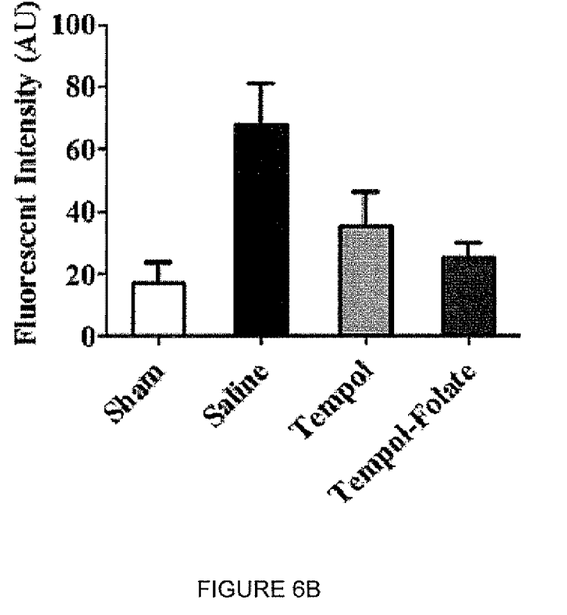
FIG. 6B shows data on quantification of fluorescent intensity of hydrocyanine-3 treated mouse kidney sections.
Figure 6C:
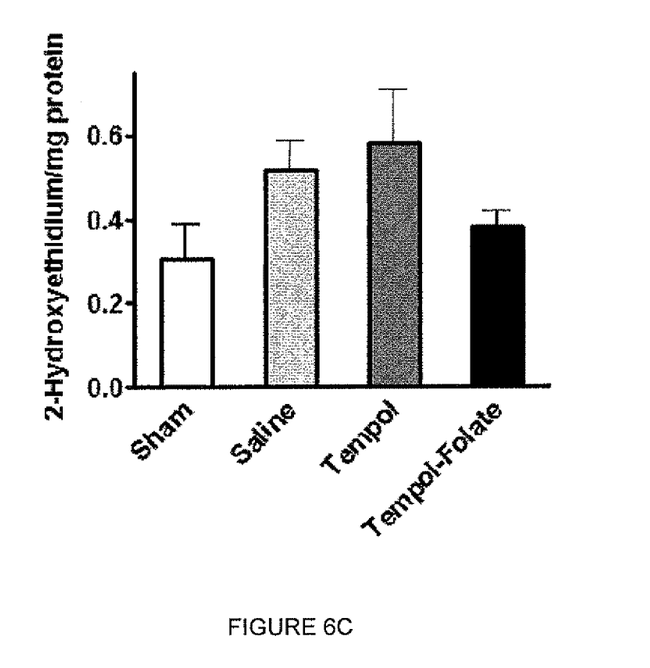
FIG. 6C shows data on whole kidney superoxide concentration measured by DHE-HPLC normalized to protein concentration, n=4.
Figure 6D:
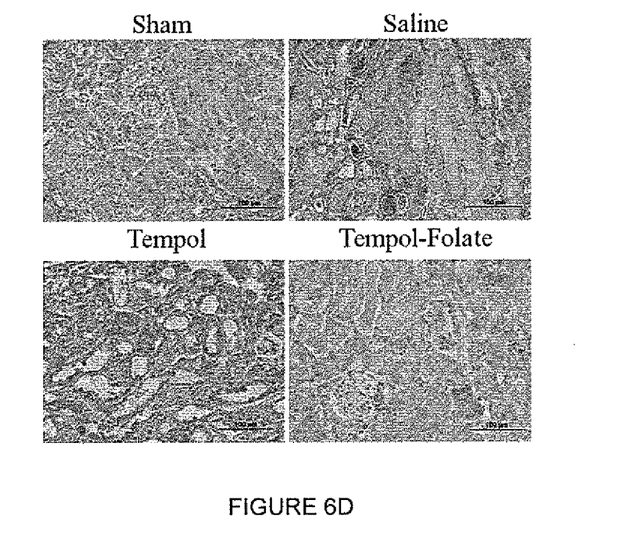
FIG. 6D shows representative nitrotyrosine staining in kidney sections 48 hours post-ischemia, images taken at 20× magnification. Data represent mean and SEM. These data show that tempol-folate is more effective at scavenging superoxide in the kidney after 30 minutes renal ischemia.
Figure 7:
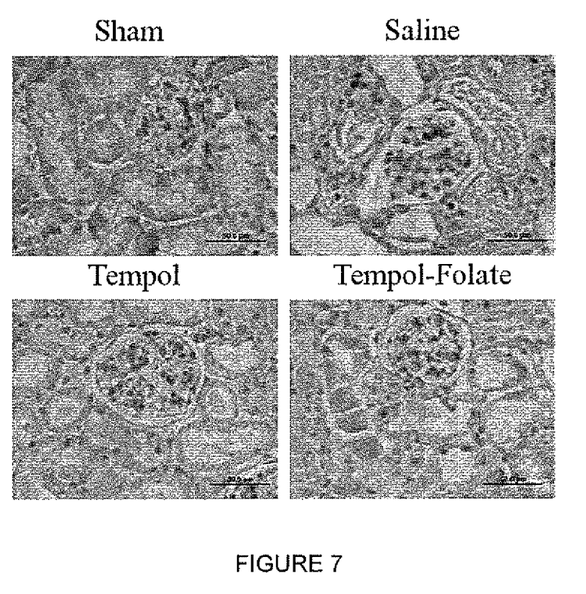
FIG. 7 shows representative hematoxylin and eosin (H&E) staining of kidney sections harvested 48 hours post-ischemia. These images display that renal structure is protected from renal ischemia-reperfusion injury by tempol-folate treatment more efficiently than by ternpol treatment.

The details of some exemplary embodiments of the methods and systems of the present disclosure are set forth in the description below. Other features, objects, and advantages of the disclosure will be apparent to one of skill in the art upon examination of the following description, drawings, examples and claims. It is intended that all such additional systems, methods, features, and advantages be included within this description, be within the scope of the present disclosure, and be protected by the accompanying claims.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. patent law and the term is open-ended, allowing for the presence of more than that which is recited so long as basic or novel characteristics of that which is recited is not changed by the presence of more than that which is recited, but excludes prior art embodiments.

Prior to describing the various embodiments, the following definitions are provided and should be used unless otherwise indicated.

Definitions

The terms "administer", "administering", or "administration", as used herein refer to either directly administering a compound or pharmaceutically acceptable salt of the compound or a composition to an animal, or administering a prodrug derivative or analog of the compound or pharmaceutically acceptable salt of the compound or composition to the animal, which can form an equivalent amount of the compound within the animal's body.

The term "subject" as used herein includes, without limitation, a human, mouse, rat, guinea pig, dog, cat, horse, cow, pig, monkey, chimpanzee, baboon, or rhesus monkey. In one embodiment, the animal is a mammal.

The term "TEMPOL" as used herein refers to the superoxide dismutase mimetic 4-hydroxy-2,2,6,6-tetramethylpiperidine 1-oxyl.

The term "folate" as used herein refers to "N-[p-[[(2-amino-4-hydroxy-6-pteridinyl) methyl]-amino]benzoyl]-L-glutamate".

A Folate-TEMPOL conjugate refers to any molecule that contains a TEMPOL moiety and a folate moiety. The Folate-TEMPOL conjugate may be in the form of a derivative prodrug or salt thereof. The TEMPOL and folate moieties are typically substituted and coupled together and separated by linking groups containing amides, esters, peptides, hydrocarbons, glycols, polyethylene glycols, or other polymeric groups and the like.

The term "oxidative stress" as used herein refers to an imbalance between the production of reactive oxygen and a biological system's ability to readily detoxify the reactive intermediates or easily repair the resulting damage. Disturbances in the normal redox state within a living cell can cause toxic effects through the production of peroxides and free radicals that damage all components of the cell, including proteins, lipids, and DNA.

In humans, oxidative stress is involved in many diseases, such as atherosclerosis, Parkinson's disease, Heart Failure, Myocardial Infarction, Alzheimer's disease, Fragile X Syndrome, and chronic fatigue syndrome, but short-term oxidative stress may also be important in prevention of aging by induction of a process named mitohormesis. Reactive oxygen species can be beneficial, as they are used by the immune system as a way to attack and kill pathogens. Reactive oxygen species are also used in cell signaling. This is dubbed redox signaling.

In chemical terms, oxidative stress is a large rise (becoming less negative) in the cellular reduction potential, or a large decrease in the reducing capacity of the cellular redox couples, such as glutathione. The effects of oxidative stress depend upon the size of these changes, with a cell being able to overcome small perturbations and regain its original state. However, more severe oxidative stress can cause cell death and even moderate oxidation can trigger apoptosis, while more intense stresses may cause necrosis.

A particularly destructive aspect of oxidative stress is the production of reactive oxygen species, which include free radicals and peroxides. Some of the less reactive of these species (such as superoxide) can be converted by oxidoreduction reactions with transition metals or other redox cycling compounds (including quinones) into more aggressive radical species that can cause extensive cellular damage. The major portion of long term effects is inflicted by damage on DNA. Most of these oxygen-derived species are produced at a low level by normal aerobic metabolism and the damage they cause to cells is constantly repaired. However, under the severe levels of oxidative stress that cause necrosis, the damage causes ATP depletion, preventing controlled apoptotic death and causing the cell to simply fall apart.

One source of reactive oxygen under normal conditions in humans is the leakage of activated oxygen from mitochondria during oxidative phosphorylation. Enzymes capable of producing superoxide are xanthine oxidase, NADPH oxidases and cytochromes P450. Hydrogen peroxide is produced by a wide variety of enzymes including several oxidases. Reactive oxygen species play important roles in cell signalling, a process termed redox signaling. Thus, to maintain proper cellular homeostasis, a balance must be struck between reactive oxygen production and consumption.

The best studied cellular antioxidants are the enzymes superoxide dismutase (SOD), catalase, and glutathione peroxidase. Less well studied (but probably just as important) enzymatic antioxidants are the peroxiredoxins and the recently discovered sulfiredoxin. Other enzymes that have antioxidant properties (though this is not their primary role) include paraoxonase, glutathione-S transferases, and aldehyde dehydrogenases.

Oxidative stress contributes to tissue injury following irradiation and hyperoxia. It is suspected to be important in neurodegenerative diseases including Lou Gehrig's disease (aka MND or ALS), Parkinson's disease, Alzheimer's disease, and Huntington's disease. Oxidative stress is thought to be linked to certain cardiovascular disease, since oxidation of LDL in the vascular endothelium is a precursor to plaque formation. Oxidative stress also plays a role in the ischemic cascade due to oxygen reperfusion injury following hypoxia. This cascade includes both strokes and heart attacks. Oxidative stress has also been implicated in chronic fatigue syndrome.

The term "effective amount" as used herein refers to an amount of a compound or pharmaceutically acceptable salt of a compound that, when administered to an animal, is effective to prevent, to at least partially ameliorate, or to cure, a condition from which the animal suffers or is suspected to suffer.

The term "pharmaceutically acceptable salt", as used herein, refers to salts derived from organic and inorganic acids of a compound described herein. Exemplary salts include, but are not limited to, sulfate, citrate, acetate, oxalate, chloride, hydrochloride, bromide, hydrobromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, napthalenesulfonate, propionate, succinate, fumarate, maleate, malonate, mandelate, malate, phthalate, and pamoate. The term "pharmaceutically acceptable salt" as used herein also refers to a salt of a compound described herein having an acidic functional group, such as a carboxylic acid functional group, and a base. Exemplary bases include, but are not limited to, hydroxide of alkali metals including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH-($C_1$-$C_6$)-alkylamine), such as N,N-dimethyl-N-(2-hydroxyethyl)amine or tri-(2-hydroxyethyl) amine; N-methyl-D-glucamine; morpholine; thiomorpholine; piperidine; pyrrolidine; and amino acids such as arginine, lysine, and the like. The term "pharmaceutically acceptable salt" also includes hydrates of a compound described herein.

The term "pharmaceutically acceptable carrier" as used herein refers to a diluent, adjuvant, excipient, or vehicle with which a heterodimeric probe of the disclosure is administered and which is approved by a regulatory agency of the Federal or a state government or listed in the U.S. Pharmacopeia or other generally recognized pharmacopeia for use in animals, and more particularly in humans. Such pharmaceutical carriers can be liquids, such as water and oils, including those of petroleum, animal, vegetable or synthetic origin, such as peanut oil, soybean oil, mineral oil, sesame oil and the like. The pharmaceutical carriers can be saline, gum acacia, gelatin, starch paste, talc, keratin, colloidal silica, urea, and the like. When administered to a patient, the heterodimeric probes and pharmaceutically acceptable carriers preferably should be sterile. Water is a useful carrier when the heterodimeric probe is administered intravenously. Saline solutions and aqueous dextrose and glycerol solutions can also be employed as liquid carriers, particularly for injectable solutions. Suitable pharmaceutical carriers also include excipients such as glucose, lactose, sucrose, glycerol monostearate, sodium chloride, glycerol, propylene, glycol, water, ethanol and the like. The present compositions, if desired, can also contain minor amounts of wetting or emulsifying agents, or pH buffering agents. The present compositions advantageously may take the form of solutions, emulsion, sustained-release formulations, or any other form suitable for use.

The term "physiologically acceptable" as used herein refers to a composition that, in contact with a cell, isolated from a natural source or in culture, or a tissue of a host, has no toxic effect on the cell or tissue.

The terms "include", "for example", "such as", and the like are used illustratively and are not intended to limit the present invention.

The terms "treating" or "treatment" as used herein refer to the treatment of a disease-state in an animal or human subject, and may include: (a) preventing the disease, abnormal physiological, anatomical, or biochemical-state from occurring in the subject, in particular, when such subject may not yet have been diagnosed as having or displaying such as state; (b) inhibiting the disease, abnormal physiological, anatomical, or biochemical-state, e.g., arresting it development; and/or (c) relieving the disease, abnormal physiological, anatomical, or biochemical-state, e.g., causing regression of the disease, abnormal physiological, anatomical, or biochemical-state until a desired endpoint is reached. Treating also includes the amelioration of a symptom of a disease (e.g., lessen the pain or discomfort), wherein such amelioration may or may not be directly affecting the disease (e.g., cause, transmission, expression, etc.).

The term "therapeutically effective amount" as used herein includes an amount of a compound according to the present disclosure that is effective when administered alone or in combination to a indication listed herein. The term "therapeutically effective amount" also includes an amount of the combination of compounds claimed that is effective to treat the desired indication. The combination of compounds is preferably a synergistic combination. Synergy, as described, for example, by Chou and Talalay, Adv. Enzyme Regul. 1984, 22:27-55, occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased effect, or some other beneficial effect of the combination compared with the individual components.

The present agents may be systemically administered, e.g., orally, in combination with a pharmaceutically acceptable excipient such as an inert diluent or an assimilable edible carrier. They may be enclosed in hard or soft shell gelatin capsules, may be compressed into tablets or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. The percentage of the compositions and preparations may, of course, be varied and may conveniently be, but not limited to, between about 1 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills or capsules may be coated with gelatin, wax, shellac or sugar and the like: A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active agent may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with several of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

While it is contemplated that the therapeutic compositions of the present disclosure are preferably administered under controlled conditions whereby the compositions are delivered to the recipient subject intravenously, it is not intended that other routes of administration are excluded, such as a bolus injection, inhalation, tablet form and the like, or directly to the renal tissues.

The amount of the agent required for use in treatment will vary not only with the particular agent selected but also with the route of administration, the nature of the condition being treated, and the age and condition of the patient and will be ultimately at the discretion of the attendant physician or clinician. In general, however, a suitable dose will be in the range of from (a) about 1.0-100 mg/kg of body weight per day, (b) about 10-75 mg/kg of body weight per day, and (c) about 5-20 mg per kilogram body weight per day.

The compounds described herein may be administered in the form of prodrugs. A prodrug can include a covalently bonded carrier which releases the active parent drug when administered to a mammalian subject. Prodrugs can be prepared by modifying functional groups present in the compounds in such a way that the modifications are cleaved, either in routine manipulation or in vivo, to the parent compounds. Prodrugs include, for example, compounds wherein a carboxylic acid group is bonded to any group that, when administered to a mammalian subject, cleaves to form a free carboxylic acid, e.g., ester of the carboxylic acid. Examples of prodrugs include, but are not limited to, ethyl or methyl esters, ethoxy or methoxy groups in place of a phenol hydroxy. Methods of structuring a compound as prodrugs can be found in the book of Testa and Mayer, Hydrolysis in Drug and Prodrug Metabolism, Wiley (2006). Typical prodrugs form the active metabolite by in vivo transformation through hydrolytic enzymes, the hydrolysis of amide, lactams, peptides, carboxylic acid esters, epoxides or the cleavage of esters of inorganic acids.

Blood Urea Nitrogen (BUN) Test

The blood urea nitrogen (BUN) test is a measure of the amount of nitrogen in the blood in the form of urea, and a measurement of renal function. Urea is a substance secreted by the liver, and removed from the blood by the kidneys.

The liver produces urea in the urea cycle as a waste product of the digestion of protein. Normal human adult blood should contain between 7 to 21 mg of urea nitrogen per 100 ml (7-21 mg/dL) of blood. Individual laboratories may have different reference ranges, and this is because the procedure may vary.

The most common cause of an elevated BUN, anorexia, is poor kidney function, although a serum creatinine level is a somewhat more specific measure of renal function (see also renal function). A greatly elevated BUN (>60 mg/dL) generally indicates a moderate-to-severe degree of renal failure. Impaired renal excretion of urea may be due to temporary conditions such as dehydration or shock, or may be due to either acute or chronic disease of the kidneys themselves.

An elevated BUN in the setting of a relatively normal creatinine may reflect a physiological response to a relative decrease of blood flow to the kidney (as seen in heart failure or dehydration) without indicating any true injury to the kidney. However, an isolated elevation of BUN may also reflect excessive formation of urea without any compromise to the kidneys. When the ratio of BUN to creatinine is greater than 20, the patient is suspected of having pre-renal azotemia. This means that the pathologic process is unlikely to be due to intrinsic kidney damage.

Because multiple variables can interfere with the interpretation of a BUN value, GFR and creatinine clearance are more accurate markers of kidney function. Age, sex, and weight will alter the "normal" range for each individual, including race. In renal failure or chronic kidney disease (CKD), BUN will only be elevated outside "normal" when more than 60% of kidney cells are no longer functioning. Hence, more accurate measures of renal function are generally preferred to assess the clearance for purposes of medication dosing. BUN is reported as mg/dL in the United States. Elsewhere, the concentration of urea is reported as mmol/L. Chemical colorimetric tests are Diacetyl Monoxime, Urograph and Modified Berthelot Enzymatic methods.

Creatinine

Creatinine is a break-down product of creatine phosphate in muscle, and is usually produced at a fairly constant rate by the body (depending on muscle mass). Chemically, creatinine is a spontaneously formed cyclic derivative of creatine. Creatinine is chiefly filtered out of the blood by the kidneys, though a small amount is actively secreted by the kidneys into the urine. There is little or no tubular reabsorption of creatinine. However, if the filtering of the kidney is deficient, blood levels rise. Therefore, creatinine levels in blood and urine may be used to calculate the creatinine clearance (CrCI), which reflects the glomerular filtration rate (GFR), The GFR is clinically important because it is a measurement of renal function. However, in cases of severe renal dysfunction, the creatinine clearance rate will be "overestimated" because the active secretion of creatinine will account for a larger fraction of the total creatinine cleared.

A more complete estimation of renal function can be made when interpreting the blood (plasma) concentration of creatinine along with that of urea. BUN-to-creatinine ratio (the ratio of urea to creatinine) can indicate other problems besides those intrinsic to the kidney; for example, a urea level raised out of proportion to the creatinine may indicate a pre-renal problem such as volume depletion.

Measuring serum creatinine is a simple test and it is the most commonly used indicator of renal function. A rise in blood creatinine levels is observed only with marked damage to functioning nephrons. Therefore, this test is not suitable for detecting early stage kidney disease. A better estimation of kidney function is given by the creatinine clearance test. Creatinine clearance can be accurately calculated using serum creatinine concentration and some or all of the following variables: sex, age, weight, and race as suggested by the American Diabetes Association without a 24 hour urine collection. Some laboratories will calculate the CrCl if written on the pathology request form; and, the necessary age, sex, and weight are included in the patient information. In the United States, creatinine is typically reported in mg/dL, while in Canada and Europe mmol/liter may be used. 1 mg/dL of creatinine is 88.4 µmol/L.

The typical human reference ranges are 0.5 to 1.0 mg/dL (about 45-90 µmol/L) for women and 0.7 to 1.2 mg/dL (60-110 µmol/L) for men. While a baseline serum creatinine of 2.0 mg/dL (150 µmol/L) may indicate normal kidney function in a male body builder, a serum creatinine of 1.2 mg/dL (110 µmol/L) can indicate significant renal disease in a frail old woman.

The term "ischemia" as used herein refers to a restriction in blood supply, generally due to factors in the blood vessels, with resultant damage or dysfunction of tissue. It may also be spelled ischaemia or ischaamia. Rather than hypoxia (a more general term denoting a shortage of oxygen, usually a result of lack of oxygen in the air being breathed), ischemia is an absolute or relative shortage of the blood supply to an organ, i.e. a shortage of oxygen, glucose and other blood-borne components. A relative shortage means the mismatch of blood supply (oxygen/fuel delivery) and blood request for adequate metabolism of tissue. Ischemia results in tissue damage because of a lack of oxygen and nutrients. Ultimately, this can cause severe damage because of the potential for a build-up of metabolic wastes. Ischemia can also be described as an inadequate flow of blood to a part of the body, caused by constriction or blockage of the blood vessels supplying it. This can be due to, but is not limited to, such as hypoglycemia (lower than normal level of blood glucose); tachycardia (abnormally rapid beating of the heart); atherosclerosis (lipid-laden plaques obstructing the lumen of arteries); hypotension (low blood pressure, e.g. in septic shock, heart failure); thromboembolism (blood clots); outside compression of a blood vessel, e.g. mechanically by pressure, severing of a blood vessel, implantation of a transplanted organ, surgery, by a tumor, and the like; embolism (foreign bodies in the circulation, e.g. amniotic fluid embolism); sickle cell disease (abnormally shaped red blood cells); induced g-forces which restrict the blood flow and force the blood to the extremities of the body, as in acrobatics and military flying; and localized extreme cold, such as by frostbite, ice, or improper cold compression therapy.

Since oxygen is mainly bound to hemoglobin in red blood cells, insufficient blood supply causes tissue to become hypoxic, or, if no oxygen is supplied at all, anoxic. In very aerobic tissues such as heart and brain, at body temperature necrosis due to ischemia usually takes about 3-4 hours before becoming irreversible. This and typically some collateral circulation to the ischemic area accounts for the efficacy of "clot-buster" drugs given for stroke and heart attack within this time period. However, complete cessation of oxygenation of such organs for more than 20 minutes typically results in irreversible damage.

Restoration of blood flow after a period of ischemia can actually be more damaging than the ischemia. Reintroduction of oxygen causes a greater production of damaging free radicals, resulting in reperfusion injury. With reperfusion injury, necrosis can be greatly accelerated. Low doses of hydrogen sulfide ($H_2S$) have been found to protect against regional myocardial ischemia-reperfusion injury.

The term "reperfusion" as used herein refers to the restoration of blood flow to a tissue following ischemia. The damage of reperfusion injury is due in part to the inflammatory response of damaged tissues. White blood cells carried to the area by the newly returning blood release a host of inflammatory factors such as interleukins as well as free radicals in response to tissue damage. The restored blood flow reintroduces oxygen within cells that damages cellular proteins, DNA, and the plasma membrane. Damage to the cell's membrane may in turn cause the release of more free radicals. Such reactive species may also act indirectly in redox signaling to turn on apoptosis. Leukocytes may also build up in small capillaries, obstructing them and leading to more ischemia.

Reperfusion injury plays a part in the brain's ischemic cascade, which is involved in stroke and brain trauma. Similar failure processes are involved in brain failure following reversal of cardiac arrest; control of these processes is the subject of ongoing research. Repeated bouts of ischemia and reperfusion injury also are thought to be a factor leading to the formation and failure to heal of chronic wounds such as pressure sores and diabetic foot ulcers. Continuous pressure limits blood supply and causes ischemia, and the inflammation occurs during reperfusion. As this process is repeated, it eventually damages tissue enough to cause a wound.

In prolonged ischemia (60 minutes or more), hypoxanthine is formed as breakdown product of ATP metabolism. The enzyme xanthine dehydrogenase acts in reverse, i.e. as a xanthine oxidase as a result of the higher availability of oxygen. This oxidation results in molecular oxygen being converted into highly reactive superoxide and hydroxyl radicals. Xanthine oxidase also produces uric acid, which may act as both a prooxidant and as a scavenger of reactive species such as peroxynitrite. Excessive nitric oxide produced during reperfusion reacts with superoxide to produce the potent reactive species peroxynitrite. Such radicals and reactive oxygen species attack cell membrane lipids, proteins, and glycosaminoglycans, causing further damage. They may also initiate specific biological processes by redox signaling.

Description

The present disclosure encompasses compositions and their uses for the prevention of ischemia-reperfusion injuries that result in oxidative stress injuries in, but not limited to, the kidney. The compositions of the disclosure provide a conjugate between TEMPOL and Folic acid (folate). In an illustrative example, the folate moiety of the conjugate is preferentially able to bind to the folate receptors of the renal proximal tubule, thereby also delivering the potent anti-oxidant to the luminal cells. The conjugate may then be internalized by the receiving cell, resulting in a reduction in the level of NO-induced free radicals that could otherwise result in oxidative damage to the cells. By preemptively administering the conjugates of the disclosure to the kidney before the formation of a ischemia, NO-induced injury that results from the subsequent reperfusion of the organ is reduced.

The discovery herein described demonstrates that the conjugate of TEMPOL and folate is more potent than folate on its own in reducing ischemic-reperfusion damage to a tissue, in this case, the kidney proximal tubules. Ischemic-induced superoxide is significantly reduced by the Folate-TEMPOL conjugate, compared to the use of TEMPOL alone. While not wishing to be bound by any one theory, the data shows that the Folate-TEMPOL conjugate has a greater affinity for proximal tubule cells than does TEMPOL alone.

The effects of the Folate-TEMPOL conjugate of the present disclosure on renal ischemic-reperfusion injury prevention were observed by intravenously administering TEMPOL or Folate-TEMPOL. The renal artery was then clamped for about 30 mins, followed by 48 hours of reperfusion. Parameters measured as indicators of renal tubule injury included creatinine, BUN, and albumin levels both before and after ischemia. Also measured were the TEMPOL and Folate-TEMPOL concentrations in the plasma and the kidney.

Conjugating folate to TEMPOL results in a marked reduction in the three parameters that, when elevated, indicate renal oxidative damage.

The data shows that Folate-TEMPOL inhibits superoxide as efficiently as TEMPOL alone, and that Folate-TEMPOL accumulates in cultured proximal tubule cells to a greater extent than un-conjugated Tempol.

Post-ischemic increases in plasma albumin, creatinine and BUN were reduced by providing the Folate-TEMPOL conjugate to the subject before the ischemia-reperfusion, and that the reduction was greater than if TEMPOL alone was used. These results indicate that Folate-TEMPOL is more effective at preventing post-ischemic renal injury than is TEMPOL, and that specifically targeting proximal tubule oxidative damage could prevent the development of renal failure as a result of ischemia-reperfusion in settings such as renal transplant.

The use of the folate conjugate reduces the anti-oxidant dose required and by targeting vulnerable sites reduces non-specific antioxidant effects. It is further contemplated that the conjugate of the present disclosure may also be used to reduce the oxidative stress damage in organs and tissues other than those of the renal system, and especially in those systems where there are folate receptors to facilitate the transport of the conjugate into the intracellular environment to inactivate the superoxide free radicals.

One aspect of the disclosure, therefore, encompasses methods for reducing oxidative stress injury of a tissue comprising: delivering to a human or animal subject a pharmaceutically acceptable composition comprising an effective amount of a Folate-TEMPOL conjugate, thereby reducing oxidative stress injury to a tissue of the human or animal subject.

In embodiments of this aspect of the disclosure, the pharmaceutically acceptable composition may further comprise a pharmaceutically acceptable carrier.

In some embodiments of the methods of this aspect of the disclosure, the oxidative stress injury to a tissue of the subject animal or human can be caused by renal ischemia.

In some embodiments of this aspect of the disclosure, the oxidative stress injury to a tissue of the subject animal or human can be caused by ischemia-reperfusion on a kidney of the subject human or animal.

In some embodiments of the methods of this aspect of the invention, the pharmaceutically acceptable composition may be delivered to the subject human or animal before the induction of oxidative stress injury to a tissue of the subject animal or human.

In some embodiments of the methods of this aspect of the invention, the pharmaceutically acceptable composition is delivered to the subject human or animal before a renal ischemia or the reperfusion thereof.

In embodiments of the methods of this aspect of the invention, the Folate-TEMPOL conjugate has the formula:

prodrugs or salts thereof, wherein n is 1 to 10, 10 to 100, 100 to 1,000, and 1,000 to 10,000.

Another aspect of the disclosure encompasses compositions comprising a pharmaceutically active Folate-TEMPOL conjugate.

In some embodiments of this aspect of the disclosure, the composition may further comprise a pharmaceutically acceptable carrier.

In some embodiments, it is contemplated that compositions disclosed herein can be administered to subject before, during or after certain medical procedures, such as, organ transplants (heart, kidneys, liver, lungs, pancreas, intestine, and thymus) or other surgeries that reduce blood flow (cardiovascular surgery). The subject may be receiving or donating the organ.

In some embodiments, it is contemplated that composition disclosed herein can be used in biological (organ, tissue, or cell) storage mediums, typically aqueous solutions maintained at or below room temperatures, which may contain other ingredients such as, but not limited to, salts (sodium chloride, sodium lactate, calcium chloride, potassium chloride), amino acids, saccharides, polysaccharides (dextran, chondroitin, hydroxyethyl starch), vitamins (thiamine, ascorbic acid, calciferol, riboflavin, pyridoxine, tocopherol, cobalamins, phylloquinone, pantothenic acid, biotin, niacin, folic acid) and/or adenosine triphosphate or precursors (adenosine, inosine, and adenine).

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and the present disclosure and protected by the following claims.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

EXAMPLES

Example 1

Synthesis of Folate-TEMPOL Conjugate (1)

The Folate-TEMPOL conjugate (1) was synthesized following modified esterification strategy described by Crich et al., (2007) J. Am. Chem. Soc. 129: 12106, (S-24-25), incorporated herein by reference in its entirety. To an oven-dried 100 mL round-bottomed flask fitted with a magnetic stir-bar and septum under nitrogen were added 4-amino-2,2,6,6-tetramethylpiperidinyloxy, free radical (0.32 g, 2.02 mmol, 1.0 equiv.), folic acid (1.00 g, 2.26 mmol, 1.0 equiv.), N-(3-dimethylaminopropyl)-N'-ethylcarbodiimide hydrochloride (0.47 g, 2.48 mmol, 1.2 equiv.) and 1-hydroxybenzotriazole (0.438 g, 0.34 mmol, 1.2 equiv.) followed by approximately 30 mL dry $CH_2Cl_2$ and 10 mL dry DMF and cooled to 0° C.

N,N-diisopropylethylamine (1.14 g, 8.82 mmol, 4.3 equiv.) was added drop-wise. The reaction mixture was then allowed to warm to room temperature and stirred overnight. The reaction mixture was diluted up with $CH_2Cl_2$, washed with saturated aqueous $NaHCO_3$ and brine and dried over $Na_2SO_4$. The solvent was evaporated and the crude radical dried under vacuum. The Folate-TEMPOL conjugate was further purified by recrystalization from ethanol.

Data regarding the activity of this Folate-TEMPOL Conjugate is provided in the figures. Typically, cultured human proximal tubule (HK-2) cells were treated with LPS to induce superoxide free radical formation. The level of superoxide is indicated by the formation of 2-hydroxyethidium as described, for example by Zielonka et al., (2008) Nat. Protocols 3: 8-21, incorporated herein by reference in its entirety.

Example 2

Synthesis of Folate-PEG-TEMPOL Conjugate (2)

One uses procedures as provided for in Zalipsky et al, FESS Letters 353 (1994) 71-74 and Esmaeili et al., Journal of Drug Targeting, (2008) 16(5): 415-423. One couples folate with a monoamino polyethylene glycol (PEG). One activates the hydroxyl of PEG the with N,N'-disuccinimidyl carbonate then reacts with 4-amino-2,2,6,6-tetramethylpiperidinyloxy, free radical.

Example 3

Synthesis of Folate-PLA-TEMPOL Conjugate (3)

One uses procedures as provided for in Zalipsky et al, FEBS Letters 353 (1994) 71-74 and Esmaeili et al., Journal of Drug Targeting, (2008) 16(5): 415-423. One couples folate with a diamino alkyl which is optionally monoamine substituted with a protecting group. Removal of the protecting group provides a folate-amine. Polylactic acid (PLA) is coupled to the amine. One activates the hydroxyl of PLA with N,1\1'-sisuccinimidyl carbonate then reacts with 4-amino-2,2,6,6-tetramethylpiperidinyloxy, free radical.

The invention claimed is:

1. A pharmaceutical composition comprising a conjugate having the formula:

or an ester of the carboxylic acid or pharmaceutically acceptable salt thereof and a pharmaceutically acceptable carrier.

2. A biological storage solution comprising a conjugate having the formula:

or an ester of the carboxylic acid or salt thereof, wherein the solution further comprising a component selected from a salt, amino acid, vitamin, a saccharide, a polysaccharide, and adenosine triphosphate or precursor.

3. A method of treating ischemic injury comprising administering a pharmaceutical composition of claim 1 to a subject.

4. The method of claim 3, wherein the subject is diagnosed with reduced kidney function.

5. The method of claim 3, wherein the subject received an organ transplant.

6. The method of claim 3, wherein the pharmaceutical composition is delivered to the subject before, after, or during a medical procedure.

* * * * *